United States Patent [19]

Takekoshi et al.

[11] Patent Number: 5,015,703
[45] Date of Patent: May 14, 1991

[54] REACTIVELY CAPPED POLYARYLENE SULFIDE AND METHOD AND INTERMEDIATES FOR THEIR PREPARATION

[75] Inventors: Tohru Takekoshi, Scotia; Andrew J. Caruso; Jane M. Terry, both of Schenectady; Edwin J. Iwanowicz, Schenectady, all of N.Y.

[73] Assignee: General Electric Company, Schenectady, N.Y.

[21] Appl. No.: 614,967

[22] Filed: Nov. 19, 1990

Related U.S. Application Data

[60] Continuation of Ser. No. 438,141, Nov. 17, 1989, abandoned, Division of Ser. No. 373,080, Jun. 29, 1989, abandoned.

[51] Int. Cl.$^5$ .............................................. C08G 75/02
[52] U.S. Cl. ...................................... 525/537; 528/481
[58] Field of Search ........................................ 525/537

[56] References Cited

U.S. PATENT DOCUMENTS

| | | | |
|---|---|---|---|
| 3,793,256 | 2/1974 | Scoggin | 528/388 |
| 4,535,149 | 8/1985 | Ebert et al. | 528/388 |
| 4,605,713 | 8/1986 | Heitz et al. | 525/537 |
| 4,605,732 | 8/1986 | Heitz et al. | 525/537 |
| 4,769,424 | 9/1988 | Takekoshi et al. | 525/537 |
| 4,820,801 | 4/1989 | Inoue et al. | 528/388 |
| 4,877,851 | 10/1989 | Fagerburg et al. | 525/537 |

FOREIGN PATENT DOCUMENTS 241961 10/1987 Japan .

OTHER PUBLICATIONS

R. T. Hawkins, *Macromolecules*, 9, "Chemistry of the Cure of Poly(p-Phenylene Sulfide)", pp. 189–194.

*Primary Examiner*—Melvyn I. Marquis
*Assistant Examiner*—David W. Woodward
*Attorney, Agent, or Firm*—William H. Pittman; James C. Davis, Jr.

[57] ABSTRACT

Polyarylene sulfides react with disulfides containing reactive functional groups, typically at temperatures within the range of about 225°–375° C., yielding reactively capped polyarylene sulfides. The preferred reactive functional groups are amino groups and carboxy groups and functional derivatives thereof.

8 Claims, No Drawings

REACTIVELY CAPPED POLYARYLENE SULFIDE AND METHOD AND INTERMEDIATES FOR THEIR PREPARATION

This application is a continuation of application Ser. No. 07/438,141, filed Nov. 17, 1989; which is a divisional of Ser. No. 07/373,080 filed June 29, 1989.

This invention relates to polyarylene sulfides, and more particularly to the reactive capping thereof.

Polyarylene sulfides, as illustrated by polyphenylene sulfide are crystalline engineering thermoplastics with high crystalline melting temperatures, typically on the order of 285° C. They are characterized by such advantageous properties as high modulus and excellent resistance to aggressive chemicals and solvents.

However, the glass transition temperatures of polyarylene sulfides are low; for example, that of polyphenylene sulfide is only 85° C. As a consequence, heat distortion temperatures are low in the absence of reinforcement with fillers such as glass fiber. For example, the heat distortion temperature of polyphenylene sulfide is about 110° C. In addition, polyarylene sulfides are very brittle, as evidenced by a tensile elongation for polyphenylene sulfide no greater than about 2.5% and frequently below 1%.

It has been proposed to improve the properties of polyarylene sulfides by blending with other polymers having properties such as high heat distortion temperature and good ductility. In preparing such blends, the presence of a compatibilizing copolymer is often advantageous. Thus, for example, blends of polyarylene sulfides and polyetherimides can be compatibilized by incorporating therein a polyarylene sulfide-polyetherimide copolymer.

U.S. Pat. No. 4,769,424 describes the preparation of polyarylene sulfide-polyetherimide block copolymers from reactively capped, particularly amine and cyclic anhydride-capped polyarylene sulfides. These capped polyarylene sulfides are prepared by a series of reactions beginning with a halogen-terminated polymer. While this method of making block copolymers is effective, it frequently requires a number of chemical reactions and is cumbersome to perform. Therefore, there is a continuing need for relatively simple methods to prepare reactively capped polyarylene sulfides.

In one of its aspects, the invention is a method for preparing a reactively capped polyarylene sulfide which comprises effecting reaction between a polyarylene sulfide and a disulfide of the formula $$A^1-S-S-A^2, \quad (I)$$

wherein:
each of $A^1$ and $A^2$ is independently

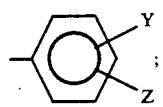

(II)

one of Y and Z is X or $-R^1X_n$ and the other is hydrogen, X or $-R^1X_n$, or Y and Z together are

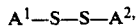

$R^1$ and $R^2$ are organic radicals;
X is a reactive functional group; and
n is 1 or 2.

The polyarylene sulfides employed in the method of this invention are known polymers containing arylene groups separated by sulfur atoms. They include polyphenylene sulfide (hereinafter sometimes designated "PPS") and substituted polyphenylene sulfides. By reason of its availability and relatively low cost, PPS is often preferred.

It is often impracticable to determine the molecular weight of a polyarylene sulfide, by reason of its insolubility in essentially all solvents used for molecular weight determination. Indirect characterization of relative molecular weight by melt flow characteristics is commonly employed. For the purposes of this invention, the melt flow characteristics of the polyarylene sulfide are not critical; values in the range of about 50-175 g./10 min. (300° C., 5 kg. load) are typical. However, it will be explained hereinafter that the method of the invention results in cleavage of the polyarylene sulfide chain, so the melt flow of the polymer used as reactant should often be less than the value desired in the product.

Also employed in the method of this invention is a disulfide of formula 1. The $A^1$ and $A^2$ values therein each independently have formula II; that is, both symmetrical and asymmetrical disulfides may be employed. Symmetrical disulfides are generally preferred. In formula II, the Y and Z radicals may be in the ortho, meta or para positions with respect to the disulfide group. Compounds in which Y and Z are in the meta and para positions are usually preferred.

Thus, the preferred disulfides may be represented by the formula

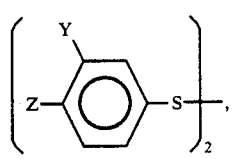

(III)

wherein Y and Z are as previously defined. Frequently, one of Y and Z is a reactive functional group (X) and the other is hydrogen.

By "reactive functional group" is meant any group capable of reaction with a functional group in another polymer molecule to form a block copolymer. Suitable groups include hydroxy, amino, isocyanato, cyano, keto and carboxy groups. Also included are functional derivatives of carboxy groups, including anhydride, halide, ester, amide and imide groups. Carboxylic acid groups and functional derivatives thereof and amine groups are preferred. Thus, illustrative disulfides are 4,4'-dithiobisbenzeneamine, hereinafter designated bis(4-aminophenyl) disulfide, and bis(3,4-dicarboxyphenyl) disulfide and its dianhydride, bis-imides and esters.

It is also within the scope of the invention for Y, Z or the combination thereof to be an organic radical containing a reactive functional group of the type defined above. A wide variety of organic radicals may be present; they include aliphatic, alicyclic and aromatic hydrocarbon radicals, substituted derivatives thereof (in which the substituents are other than the above-described reactive functional groups—for example, hetero atoms or carbonyl groups) interpolated in a chain or ring otherwise consisting of hydrocarbon groups. Aromatic radicals are often preferred, with phenylene and benzophenone-derived radicals frequently being especially preferred. Thus, the invention includes the employment of such disulfide compounds as 4,4'bis(4-carboxyphthalimidophenyl) disulfide, 4,4'-bis[4-(3,4-dicarboxybenzoyl)phthalimidophenyl] disulfide and functional derivatives thereof.

Reaction between the polyarylene sulfide and the disulfide typically occurs at temperatures in the range of about 225°–375° C. It may be conducted either in solution or in the melt, with solution reactions frequently occurring at somewhat lower temperatures than melt reactions. Thus, reaction between PPS and various disulfides in 1-chloronaphthalene as solvent takes place at temperatures on the order of 225°–270° C., while melt reactions may require temperatures of at least 300° C. Nevertheless, melt reactions are frequently preferred for at least two reasons: the convenience of conducting the reaction in equipment such as an extruder which is normally available in polymer manufacturing and processing operations, and the difficulty of recovering the products of reactions conducted in solvents which are capable both of dissolving polyarylene sulfides and of surviving the high temperatures required. It is, of course, possible to conduct the reaction under pressure in a lower boiling solvent, but this may be cumbersome and is not generally preferred.

The proportions of polyarylene sulfide and disulfide are not critical. However, it should be understood that the reaction occurs with chain cleavage of the polyarylene sulfide, and that the use of relatively large proportions of disulfide may cause cleavage into fractions having a molecular weight too low for convenience. It is generally preferred to employ about 0.1–10% by weight of disulfide, based on polyarylene sulfide.

It is known that polyarylene sulfides can be "cured" by heating in contact with an oxygen-containing gas (usually air) at temperatures above about 200° C., resulting in a substantial decrease in melt flow and, apparently, a concomitant increase in molecular weight. While the exact nature of the curing reaction is not known, it appears to involve branching and/or chain extension, probably by oxidation of some type. The reactively capped polyarylene sulfides produced by the method of this invention may also be cured without losing their functionality. Typical curing conditions are temperatures in the range of about 250°–275° C. and time periods of about 2-6 hours.

The precise mechanism of the reaction which takes place according to this invention is not known. In many respects, it appears to resemble the homolytic reaction described in Hawkins, *Macromolecules*, 9, 1989 (1976), resulting similarly in chain cleavage followed by end-capping of the polyarylene sulfide with moieties derived from the disulfide. It is possible, however, that a branching mechanism similar to that described for the aforementioned curing operation also occurs, resulting in the presence of moieties derived from the disulfide as substituents on the polyarylene sulfide chain. When used herein, therefore, the term "capped" includes the presence of such groups along the chain as well as on the ends thereof.

Another aspect of the invention is reactively capped polyarylene sulfides characterized by the presence of attached groups of the formula

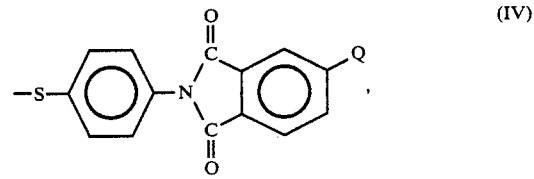

wherein Q is a carboxy group, a mono- or polycarboxy-substituted organic radical, or a functional derivative thereof. They may be prepared by the reaction of a polyarylene sulfide with a bis(imidoaryl) disulfide of the formula

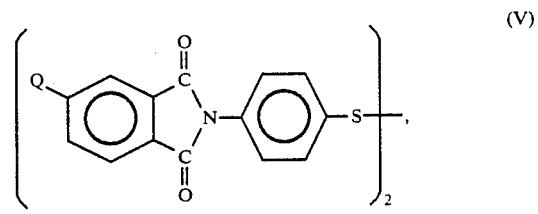

wherein Q is as previously defined.

Such bis(imidoaryl) disulfides are still another aspect of the invention. They may in turn be prepared by the reaction of bis(4-aminophenyl) disulfide with a corresponding substituted phthalic acid or anhydride in the presence of an acidic catalyst, typically a carboxylic acid such as acetic acid, phenol or m-cresol.

The invention is illustrated by the following examples. The polyarylene sulfide employed in each example was a polyphenylene sulfide having a melt flow of 71 g./10 min. at 300° C. and 5 kg. load.

EXAMPLE 1

A mixture of 62.58 grams (252 mmol.) of bis(-4aminophenyl) disulfide, 96.84 grams (504 mmol.) of trimellitic anhydride and 400 ml. of glacial acetic acid was heated under reflux for 2½ hours, with stirring and removal of water and acetic acid by distillation. An additional 200 ml. of acetic acid was added and the vessel was fitted with a trap filled with 4A molecular sieves, and refluxing was continued for 1½ hours. Upon filtration, a yellow crystalline solid was obtained; after washing with acetic acid and drying, the yield of product was 143 grams (95.1% of theoretical). Mass spectrometric analysis showed the product to comprise principally 4,4'-bis(4-carboxyphthalimidophenyl) disulfide, with a small proportion of the corresponding trisulfide. The pure disulfide was obtained by recrystallization from dimethylacetamide; it melted at 318°–319° C.

EXAMPLE 2

A mixture of 23.91 grams (96.3 mmol.) of bis(4-aminophenyl) disulfide, 100 ml. of toluene and 247 ml. of m-cresol was stirred at room temperature and 124.07 grams (385.1 mmol.) of 3,3',4,4'-tetracarboxybenzophenone dianhydride and 147 ml. of toluene were added over20 minutes, with continued stirring. A further 50 ml. of toluene and 50 ml. of m-cresol were added and the mixture was heated under reflux for 2 hours, with partial distillation of the toluene. The vessel was then fitted with a trap filled with 4A molecular sieves and heating was continued for 1 hour. The mixture was poured into 2 liters of toluene and the solid which precipitated was separated by filtration and washed with toluene and several times with acetone. The desired 4,4-bis[4-(3,4-dicarboxybenzoyl)phthalimidophenyl] disulfide dianhydride was obtained in the amount of 66.83 grams (86.4% of theoretical. It melted at 160°–180° C.

EXAMPLE 3

A solution of 124.65 grams (387 mmol.) of benzophenone-3,3',4,4'-tetracarboxylic acid dianhydride in 400 ml. of o-dichlorobenzene was heated at 180° C. as 24.02 grams (96.7 mmol.) of bis(4-aminophenyl) disulfide and 100 ml. of o-dichlorobenzene were added portionwise. The mixture was heated under reflux for 2 hours with removal of water by distillation.

Upon cooling the solution to room temperature, a solid separated which was collected by filtration, washed with cyclohexane and dried. It was heated under reflux with excess methanol and cooled, whereupon it again precipitated. The precipitate was removed by filtration and washed with methanol, yielding 77.66 grams (98% of theoretical) of the desired 4,4'-bis[4-(3,4-dicarboxybenzoyl)phthalimidophenyl] disulfide dimethyl ester. Elemental analysis showed the presence of 6.8% sulfur (theoretical amount 7.0%).

EXAMPLE 4

An intimate mixture of 5 grams of PPS in fine powder form and 250 mg. of bis(4-aminophenyl) disulfide was purged with nitrogen, heated at 350° C. for 6 minutes with mechanical stirring and cooled. The product was dissolved in 15 ml. of 1-chloronaphthalene at 230° C., cooled to room temperature and extracted with chloroform in a Soxhlet extractor, leaving as the residue 4.81 grams (96% of theoretical) of a solid which was shown by Fourier transform infrared spectroscopy and elemental analysis to be the desired amino-phenyl-terminated PPS, containing a proportion of amino functionality corresponding to 71% of the bis(4-aminophenyl) disulfide employed.

EXAMPLE 5

Three reactively capped PPS compositions were prepared using 1.52%, 0.5% and 0.1%, respectively, of bis(4-aminophenyl) disulfide. Preparation was by melt blending in a counterrotating twin screw extruder at 400 rpm., at temperatures in the range of 135°–302° C. The compositions prepared from 0.5% and 0.1% disulfide were easily stranded, affording somewhat brittle, wire-like strands. The composition prepared from 1.52% disulfide was stranded with difficulty.

Each composition was cured by heating at 260° C. in a forced air oven. A pronounced decrease in melt flow was noted with cure times greater than 1 hour; optimum melt flow conditions were obtained at curing times of 4–6 hours.

Samples comprising about 100 mg. of each uncured and cured composition were placed between two pieces of polytetrafluoroethylene-coated foil held between two stainless steel plates, placed in a Carver press preheated to 300°–310° C., equilibrated for 1 minute and pressed at 1050 kg./cm.$^2$. The pressure was released and the polymer and foil sheets were immediately quenched in a water bath to prevent crystallization of the PPS chains, after which they were subjected to quantitative infrared analysis which showed, in each instance, the presence of amino groups. It is thus apparent that the amine functionality was not lost upon curing, although the proportion thereof decreased slightly.

EXAMPLE 6

A mixture of 10 grams of PPS and 401 mg. of the disulfide of Example 1 was heated with 1-chloronaphthalene at 250° C. for 2 hours, with stirring. The solution was cooled and the precipitated polymer was filtered, washed with acetone and dried; total yield was 94.6% of theoretical.

A portion of the polymer was compression molded and quenched as described in Example 5. The Fourier transform infrared spectrum thereof showed the presence of imide and carboxylic acid groups. Upon comparison with a standard of known functionality, it was found that 41% of the carboxylic acid functionality was attached to PPS chains.

EXAMPLE 7

A mixture of 1.998 grams of PPS and 80 mg. of the disulfide of Example 1 was thoroughly blended and heated in a screw-capped test tube under nitrogen at 310° C. for 10 minutes, after which the test tube was quenched in cold water. The product was dissolved in 1-chloronaphthalene at 220° C., precipitated by cooling the solution and removed by filtration. Infrared spectroscopic analysis before and after extraction with dimethylacetamide showed that 100% of the carboxy functionality was attached to PPS chains.

EXAMPLE 8

A mixture of 750 grams of PPS and 15 grams of the disulfide of Example 1 was extruded on a single-screw extruder at temperatures in the range of 270°–290° C. The extrudate, a brittle brown solid, was shown by Fourier transform infrared spectroscopy to contain carboxyphthalimido groups.

EXAMPLE 9

The procedure of Example 8 was repeated, employing 1.5 kg. of PPS and 15 grams of the disulfide. The extrudate had a lower melt flow value, was less brittle than that of Example 8 and could be continuously stranded and cut into pellets.

EXAMPLE 10

A solid mixture of 2 grams of PPS and 79 mg. of the disulfide of Example 2 was heated in a nitrogen atmosphere at 310° C. for 10 minutes, and was then rapidly cooled by dipping in cold water. The product was dissolved in 15 ml. of 1-chloronaphthalene at 220° C., immediately cooled, washed with acetone and dried in vacuum at 80° C.

A portion of the product was compression molded as described in Example 5. A Fourier transform infrared spectrum thereof showed the presence of imide and anhydride carbonyl groups.

A second portion was extracted with dimethylacetamide in a Soxhlet extractor and similarly molded and analyzed. A comparison of the imide band with that of the unextracted material indicated 100% functionalization.

EXAMPLE 11

A mixture of 1.5 kg. of PPS and 30 grams of the disulfide of Example 3 was extruded on a single-screw extruder at temperatures in the range of 300°–314° C. A portion of the extrudate was pulverized and extracted with dimethylacetamide for 7 hours in a Soxhlet extractor, after which it was analyzed by Fourier transform infrared spectroscopy which indicated 96% functionalization.

The product was cured by heating in a forced air oven for 3 hours at 260° C., causing a decrease in melt flow from 140 to 100 g./10 min. This decrease is an indication of an increase in molecular weight.

Compositions prepared by the method of this invention which contain amino groups, such as those of Examples 4 and 5, are capable of reaction with anhydride-terminated polyetherimides to form block copolymers. Such copolymers can also be formed by the reaction of a mixture of said composition and a diamine with a tetracarboxylic acid dianhydride. Reactions of this type are disclosed in the aforementioned U.S. Pat. No. 4,769,424. A similar reaction of dicarboxy-capped polyarylene sulfides and functional derivatives thereof, such as the products of Examples 8–11, is undergone under similar conditions with amine-terminated polyetherimides or, in combination with tetracarboxylic acids or their functional derivatives, with diamines, to produce similar block copolymers.

Monocarboxy-capped polyarylene sulfides, such as the products of Examples 6 and 7, are capable of undergoing reaction with various epoxy-functionalized polymers to produce copolymers.

What is claimed is:

1. A method for preparing a cured polyarylene sulfide which comprises
   (1) effecting reaction in the melt, in the absence of solvents, between a polyarylene sulfide and a disulfide of the formula $$A^1—S—S—A^2, \quad (I)$$

wherein:
   each of $A^1$ and $A^2$ is independently

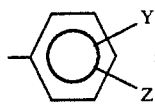

(II)

Y is X or $—R^1X_n$ and Z is hydrogen, X or $—R^1X_n$, or Y and Z together are

$R^1$ and $R^2$ are organic radicals;
   X is a functional group capable of reaction with a functional group in another polymer molecule to form a block copolymer; and
   n is 1 or 2, to form a reactively capped polyphenylene sulfide; and
   (2) heating said reactively capped polyarylene sulfide with an oxygen-containing gas at a temperature above about 200° C. for a period of time to result in a substantial decrease in melt flow.

2. A method according to claim 1 wherein the disulfide has the formula

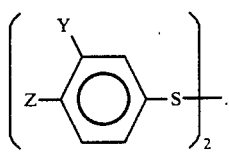

(III)

3. A method according to claim 2 wherein the curing reaction is conducted at a temperature in the range of about 250°–275° C. for a period of about 2–6 hours.

4. A method according to claim 3 wherein the polyarylene sulfide is polyphenylene sulfide.

5. A method according to claim 4 wherein X is a hydroxy, amino, isocyanato, cyano, keto or carboxy group on an anhydride, halide, ester, amide or imide derivative of a carboxy group.

6. A method according to claim 5 wherein the disulfide is bis(4-aminophenyl) disulfide.

7. A method according to claim 5 wherein the disulfide is 4,4'-bis(4-carboxyphthalimidophenyl) disulfide.

8. A method according to claim 5 wherein the disulfide is 4,4'-bis[4-(3,4-dicarboxybenzoyl)phthalimidophenyl] disulfide or a functional derivative thereof.

* * * * *